United States Patent
Barcelo et al.

(10) Patent No.: US 9,442,071 B2
(45) Date of Patent: Sep. 13, 2016

(54) APPARATUS FOR PERFORMING A SENSING APPLICATION

(75) Inventors: Steven Barcelo, Palo Alto, CA (US);
Zhiyong Li, Foster City, CA (US);
Alexandre M. Bratkovski, Mountain View, CA (US); Ansoon Kim, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 50 days.

(21) Appl. No.: 14/394,287

(22) PCT Filed: Apr. 24, 2012

(86) PCT No.: PCT/US2012/034786
§ 371 (c)(1),
(2), (4) Date: Oct. 14, 2014

(87) PCT Pub. No.: WO2013/162514
PCT Pub. Date: Oct. 31, 2013

(65) Prior Publication Data
US 2015/0116706 A1     Apr. 30, 2015

(51) Int. Cl.
*G01J 3/44* (2006.01)
*G01B 11/16* (2006.01)
*G01N 21/00* (2006.01)
*G01N 33/566* (2006.01)
(Continued)

(52) U.S. Cl.
CPC ............ *G01N 21/658* (2013.01); *B82Y 15/00* (2013.01)

(58) Field of Classification Search
CPC ............... B82Y 15/00; G01N 21/658; G01N 2201/06113; G01N 21/47; G01N 2201/068; G01N 21/648; G01N 21/6428; G01N 2021/6441; G01J 3/4412; Y10S 977/02; G02B 5/10; A61F 2/02; A61F 2/82
USPC ................ 356/301, 72, 73, 33, 32; 436/501; 250/453.11; 422/69
See application file for complete search history.

(56) References Cited

U.S. PATENT DOCUMENTS 6,174,677 B1   1/2001  Vo-Dinh
6,908,760 B2   6/2005  Cima et al.
(Continued)

FOREIGN PATENT DOCUMENTS

WO      WO-0125757      4/2001

OTHER PUBLICATIONS

Yuling Wang, et al,, "SERS aptasensor from nanorod-nanoparticle junction for protein detection", Chemical Communications, 2010,46, p. 613-615.

*Primary Examiner* — Tarifur Chowdhury
*Assistant Examiner* — Sunghee Y Gray
(74) *Attorney, Agent, or Firm* — Mannava & Kang, P.C.

(57) ABSTRACT

An apparatus for performing a sensing application includes a reservoir to contain a solution, a dispenser to dispense the solution from the reservoir, and a substrate having a plurality of nano-fingers positioned to receive the dispensed solution, in which the plurality of nano-fingers are flexible, such that the plurality of nano-fingers are configurable with respect to each other. The apparatus also includes an illumination source to illuminate the received solution, an analyte introduced around the plurality of nano-fingers, and the plurality of nano-fingers, in which light is to be emitted from the analyte in response to being illuminated. The apparatus further includes a detector to detect the light emitted from the analyte.

14 Claims, 7 Drawing Sheets

(51) Int. Cl.
  *G01N 30/96* (2006.01)
  *G01N 21/65* (2006.01)
  *B82Y 15/00* (2011.01)

(56) References Cited

U.S. PATENT DOCUMENTS

| | | |
|---|---|---|
| 7,267,948 B2 | 9/2007 | Vo-Dinh |
| 7,351,588 B2 | 4/2008 | Poponin |
| 7,812,938 B2 | 10/2010 | Guo et al. |
| 7,869,044 B2 | 1/2011 | Wang |
| 7,982,872 B2 | 7/2011 | Sardashti et al. |
| 2002/0160521 A1 | 10/2002 | Ozbal et al. |
| 2003/0170732 A1* | 9/2003 | Yogi .............. B01L 3/508 435/7.1 |
| 2005/0003458 A1 | 1/2005 | Moore et al. |
| 2008/0174775 A1* | 7/2008 | Moskovits ........ G01N 21/658 356/301 |
| 2009/0002699 A1* | 1/2009 | Sutherland ........ B82Y 15/00 356/301 |
| 2010/0040979 A1 | 2/2010 | Weimer |
| 2011/0077480 A1* | 3/2011 | Bloom ............. A61B 5/1427 600/310 |
| 2011/0212512 A1* | 9/2011 | Wang ............... B82Y 20/00 435/288.7 |
| 2012/0092660 A1 | 4/2012 | Wu et al. |

* cited by examiner

APPARATUS FOR PERFORMING A SENSING APPLICATION

BACKGROUND

Raman scattering optical spectroscopy employs an emission spectrum or spectral components thereof produced by inelastic scattering of photons by an internal structure of the material being illuminated. These spectral components contained in a response signal (for instance, a Raman signal) are to facilitate determination of the material characteristics of an analyte species including identification of the analyte.

The Raman signal level or strength is often significantly enhanced by using a Raman-active material (for instance, Raman-active surface), however. For instance, the Raman scattered light generated by a compound (or ion) adsorbed on or within a few nanometers of a structured metal surface can be $10^3$-$10^{12}$ times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection.

BRIEF DESCRIPTION OF THE DRAWINGS

Features of the present disclosure are illustrated by way of example and not limited in the following figure(s), in which like numerals indicate like elements, in which.

DETAILED DESCRIPTION

Figure 1A:
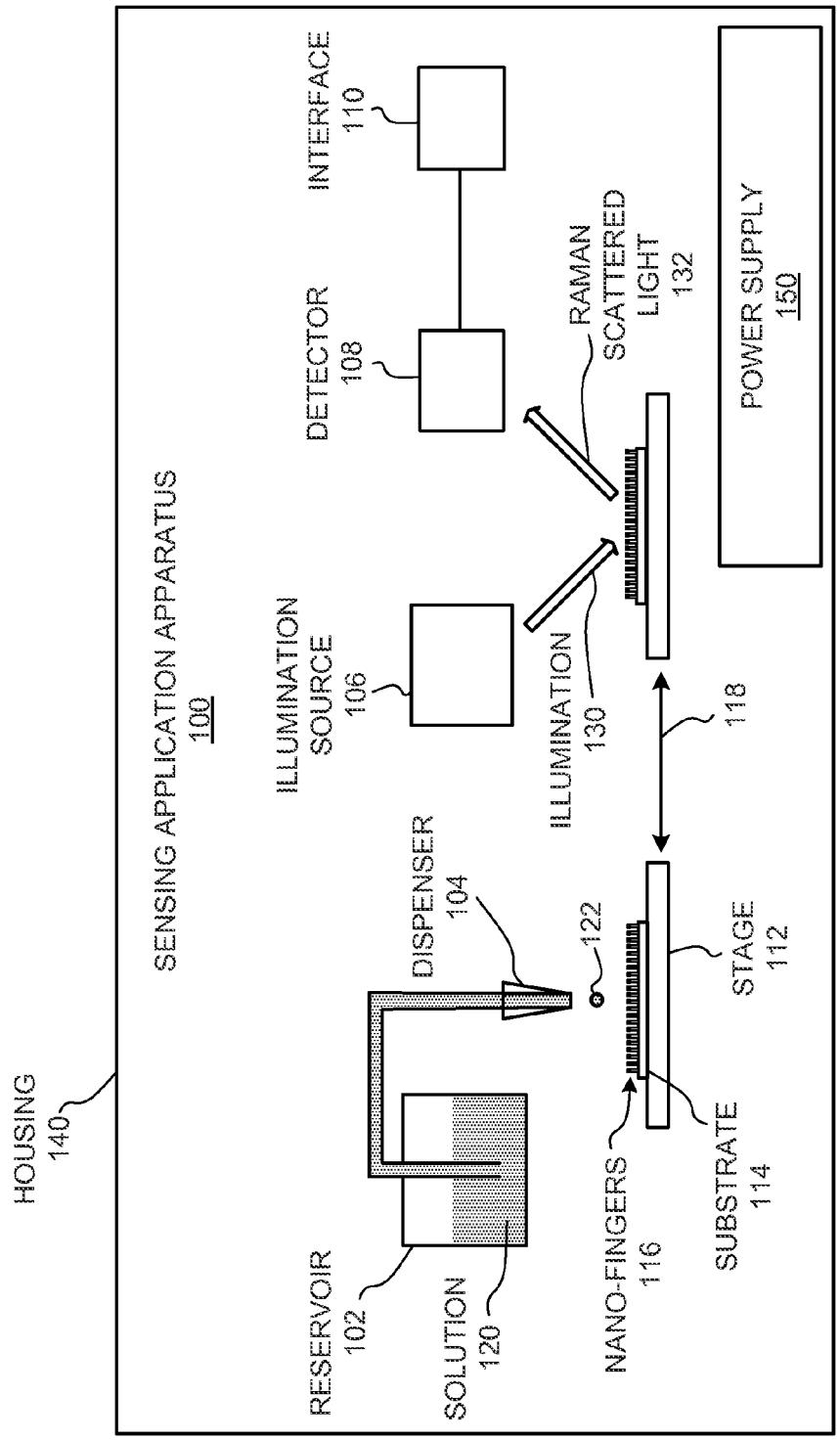
FIGS. 1A-1C, respectively, show simplified cross-sectional side views of apparatuses for performing a sensing application, according to examples of the present disclosure.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on. In addition, the term "light" refers to electromagnetic radiation with wavelengths in the visible and non-visible portions of the electromagnetic spectrum, including infrared and ultra-violet portions of the electromagnetic spectrum.

Disclosed herein are an apparatus and a method for performing a sensing application, such as, SERS, enhanced luminescence, enhanced fluorescence, etc. The apparatus includes a reservoir, a dispenser to dispense a solution contained in the reservoir, a substrate having a plurality of nano-fingers positioned to receive the dispensed solution, an illumination source, and a detector. The nano-fingers are flexible, such that, the nano-fingers are configurable with respect to each other. In one regard, the nano-fingers may have a first configuration prior to a measurement being made and a second, different configuration during performance of the measurement. The illumination source is to illuminate the received solution, an analyte introduced around the plurality of nano-fingers, and the plurality of nano-fingers. In addition, the detector, which may comprise a spectrometer, is to detect light, such as, Raman scattered light, emitted from the analyte in response to being illuminated by light from the illumination source. The detector is also to convert the detected light into electrical signals representative of the detected light. The apparatus may also include an interface through which the electrical signals are communicated. The interface comprises a wireless and/or wired interface.

Generally speaking, the apparatus disclosed herein performs both the collection and measurement of an analyte and thus, the apparatus may be used outside of a laboratory environment. In addition, because the electrical signals representative of the detected Raman scattered light are communicated externally to the apparatus, a device external to the apparatus may perform relatively complicated operations, such as, processing of the detected Raman scattered light. As such, the apparatus disclosed herein may have a relatively small and compact form factor and may thus suitable for hand-held use as well as for deployment in the field. In addition, the sensing application apparatus disclosed herein may be fabricated at a relatively lower cost as compared with sensing equipment that also perform processing of detected Raman scattered light.

With reference first to FIG. 1A, there is shown a simplified cross-sectional side view of an apparatus 100 for performing a sensing application, according to an example. It should be understood that the apparatus 100 depicted in FIG. 1A may include additional elements and that some of the elements described herein may be removed and/or modified without departing a scope of the apparatus 100. It should also be understood that the elements depicted in FIG. 1A are not drawn to scale and thus, the elements may have different relative sizes with respect to each other than as shown therein.

The apparatus 100 is depicted as including a reservoir 102, a dispenser 104, an illumination source 106, a detector 108, an interface 110, a stage 112, a substrate 114, and a plurality of nano-fingers 116. The components of the sensing application apparatus 100 are further depicted as being integrated into a single housing 140. In this regard, the sensing application apparatus 100 may be fabricated as a portable, hand-held device. That is, the housing 140 may be sized such that a user may carry the apparatus 100 in one or both hands. By way of particular example, the housing 140 may be less than about 12 inches wide by about 12 inches long by about 4 inches high. In addition, although not shown, the housing 140 may comprise an opening through which samples containing analytes, such as, air, water, etc., from a surrounding environment, may be introduced into the housing 140 for testing.

As discussed in greater detail herein below, the plurality of nano-fingers 116 are flexible to cause tips of adjacent ones of some of the plurality of nano-fingers 116 to be drawn toward each other. In addition, and according to an example, Raman-active material nano-particles (not labeled in FIG. 1A) are provided at least on the tips of the plurality of nano-fingers 116 to substantially enhance the emission of Raman scattered light from the analyte. In this regard, as the tips of the nano-fingers 116 are drawn together, the Raman-active material nano-particles provided on the tips of some of the adjacent nano-fingers 116 may be drawn toward each other such that a relatively small or no gap exists between the Raman-active material nano-particles.

A nano-finger 116 is defined, for instance, as an elongated, nanoscale structure having a length (or height) that exceeds by more than several times a nanoscale cross sectional dimension (for instance, width) taken in a plane perpendicular to the length (for instance, length>3×width). In general, the length is much greater than the width or cross sectional dimension to facilitate bending of the nano-finger 116 laterally toward one or more neighboring nano-fingers 116. In some examples, the length exceeds the cross sectional dimension (or width) by more than a factor of about 5 or 10. For example, the width may be about 100 nanometers (nm) and the height may be about 500 nm. In another example, the width at the bases of the nano-fingers 116 may range between about 10 nm and about 1 micrometer (μm) and the length may range between about 50 nm and 2 μm. In other examples, the nano-fingers 116 are sized based upon the types of materials used to form the nano-fingers 116. Thus, for instance, the more rigid the material(s) used to form the nano-fingers 116, the less the width of the nano-fingers 116 may be to enable the nano-fingers 116 to be laterally collapsible. In further examples, the nano-fingers 116 may form ridges in which two of three dimensions (for instance, length and height) exceed by more than several times a nanoscale cross sectional dimension (for instance, width). The nano-fingers 116 may equivalently be referenced as nano-poles or nano-pillars without departing from a scope of the apparatus 100.

In FIG. 1A, the reservoir 102 is also depicted as containing a solution 120 that is delivered to the dispenser 104, droplets 122 of which the dispenser 104 dispenses onto the nano-fingers 116. The dispenser 104 comprises any reasonably suitable type of dispenser that is to controllably dispense solution 120 from the reservoir 102 onto the nano-fingers 116. Thus, for instance, the dispenser 104 is to deliver a fixed volume of the solution 120 onto the nano-fingers 116 for quantitative analysis. Examples of suitable types of dispensers comprise autopippetting, thermal actuating, piezoelectric actuating, etc., types of dispensers. By way of particular example, the dispenser 104 comprises a type of dispenser that is similar to those used in inkjet printing technology. In addition, a controller (not shown) may operate the dispenser 104 to control the delivery of the droplet 122. By way of particular example, the dispenser 104 has a resolution of less than about 10 μm, but may be designed to dispense droplets 122 at various other sizes.

The solution 120 comprises any reasonably suitable type of fluid that is to be deposited onto the nano-fingers 116 and at least partially evaporated. By way of example, the solution 120 comprises a functionalized fluid that is to interact, for instance, bond with, dissolve, or have some other type of reaction with, a particular type or types of analyte molecule. As another example, the solution 120 comprises a fluid that is to be introduced into an environment containing the analyte to be tested, for instance, through intermixing of the analyte into the solution 120. As a further example, the solution 120 comprises a standard fluid of known concentration to be used in recalibrating the apparatus 100. In this regard, the reservoir 102 and in some examples, the solution 120, generally operates to collect liquid or gas samples and to store the samples prior to being deposited onto the nano-fingers 116. In addition, the reservoir 102 (and/or the solution 120) may operate to filter the samples prior to being dispensed onto the nano-fingers 116.

As also shown in FIG. 1A, the substrate 114 on which the nano-fingers 116 are provided is supported on the stage 112. According to an example, either or both of the dispenser 104 and the stage 112 is movable with respect to each other. Thus, for instance, the droplet 122 may be dispensed onto variously located nano-fingers 116 by moving the dispenser 104 and/or the stage 112 with respect to each other. In addition, the stage 112 may be moved as indicated by arrow 118 to another location within the system 100 as shown in FIG. 1A. According to an example, the nano-fingers 116 are fabricated to either be hydrophobic or hydrophilic. In this example, subsets of hydrophilic nano-fingers 116 may be separated by subsets of hydrophobic nano-fingers 116 to substantially maintain separation of the droplets 122 on the nano-fingers 116. In addition or alternatively, the substrate 114 may include alignment markers that the apparatus 100 uses to align the illumination source 106 and the detector 108 correctly such that the desired area of the substrate 114 is tested at a given time.

The illumination source 106 is further depicted as emitting electromagnetic radiation, as represented by the arrow 130, which comprises, for instance, an illumination, laser light, etc. By way of example, the illumination source 106 comprises a laser that illuminates the tips of the nano-fingers 116 as discussed in greater detail herein below. As also shown, the detector 108, which may comprise a spectrometer, captures the Raman scattered light 132. In addition, the detector 108 converts the Raman scattered light 132 into electrical signals.

Although a single illumination source 106 has been depicted in FIG. 1A, according to another example, the apparatus 100 includes an array of illumination sources 106. In this example, each of the illumination sources 106 may emit light at different wavelengths with respect to each other and a shutter system (not shown) may be incorporated into the path(s) of the illumination 130 and the Raman scattered light 132 to substantially ensure that the detector 108 is able to detect Raman scattered light 132 emitted as a result of light respectively received from the array of illumination sources 106.

According to an example, the detector 108 communicates the electrical signals to the interface 110 through which the electrical signals are to be communicated to a destination receiver (not shown). In this example, the destination receiver may store the electrical signals and/or process the electrical signals to determine, for instance, an identification of the analyte from which the Raman scattered light 132 was captured. In any regard, the interface 110 comprises hardware and/or software components that enable the electrical signals to be communicated at least one of wirelessly or through a wired connection. As such, the interface 110 may include a physical interface, such as, an Ethernet or other type of port into which a cable connector may be inserted. In addition or alternatively, the interface 110 includes a wireless interface, including an antenna, that is to communicate the electrical signals as a wireless signal, such as, as an RF signal, a Bluetooth™ signal, a WiFi™ signal, a cellular signal, etc.

According to another example, the sensing application system 100 includes components (not shown) to at least partially process the electrical signals to determine, for instance, an identification of the analyte from which the Raman scattered light 132 was captured.

The sensing application apparatus 100 is further depicted as including an optional power supply 150. The power supply 150 is considered to be optional because the sensing application apparatus 100 may be powered from electricity received through an alternating current power source. In any regard, the power supply 150 may comprise, for instance, a direct current battery or other suitable power supply. An example of a suitable power supply is a radio frequency identification (RFID) powered device. In this example, the sensing application apparatus 100 may be powered through electromagnetic radiation received, for instance, from an electromagnetic radiation source (not shown).

Figure 1B:
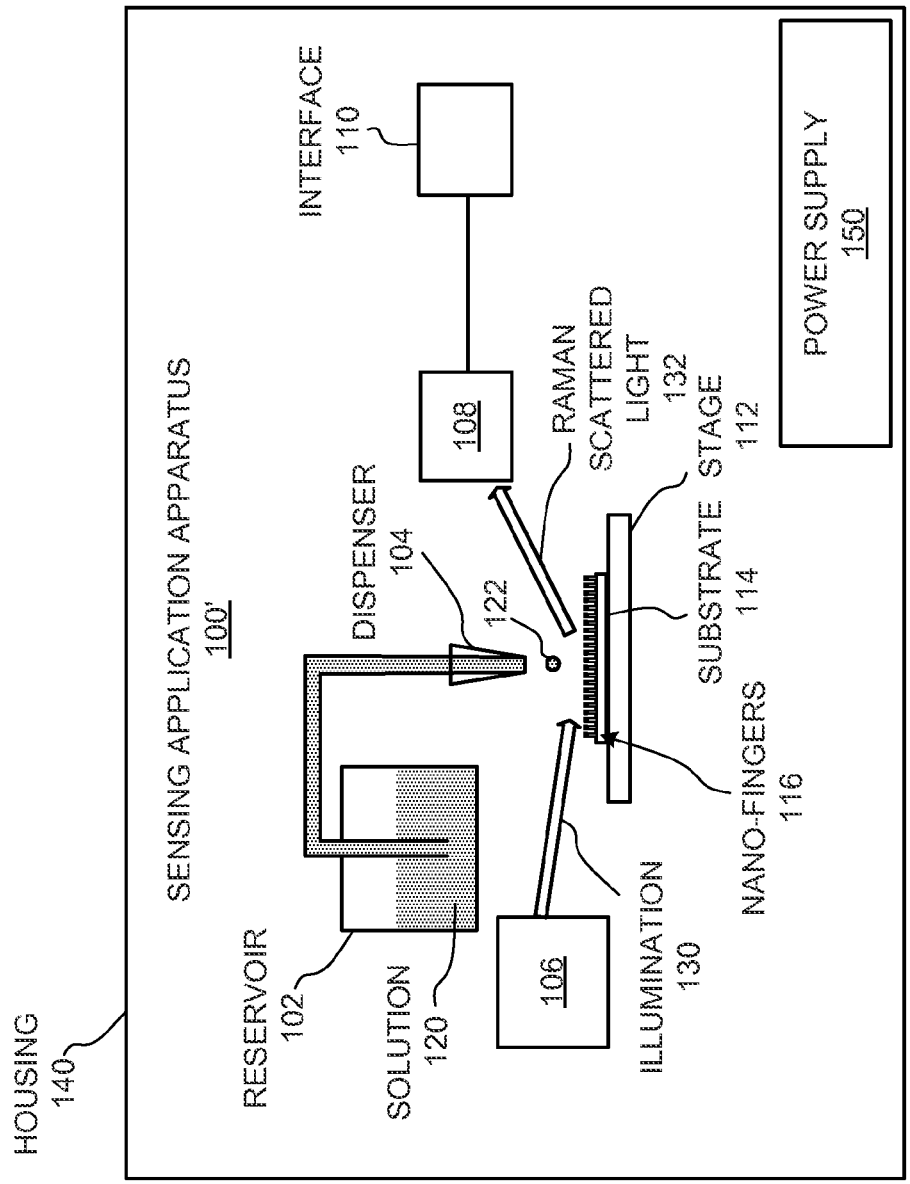

Turning now to FIG. 1B, there is shown a simplified cross-sectional side view of an apparatus 100' for performing a sensing application, according to another example. The apparatus 100' depicted in FIG. 1B includes many of the same components as those contained in the apparatus 100 depicted in FIG. 1A. As such, only those features in FIG. 1B that differ from those of FIG. 1A are described with respect to the apparatus 100'.

As shown in FIG. 1B, the illumination source 106 and the detector 108 are positioned to illuminate the nano-fingers 116 and to collect the Raman scattered light 132 without requiring that the stage 112 substantially move from a position beneath the dispenser 104. The apparatus 100' may thus have a relatively smaller size as compared with the apparatus 100 depicted in FIG. 1A. In addition, the apparatus 100' requires less moving elements as compared with the apparatus 100 depicted in FIG. 1A.

As discussed above with respect to FIG. 1A, the stage 112 may however be movable with respect to the dispenser 104 or vice versa to enable droplets 122 of the solution 120 to be deposited on variously located subsets of nano-fingers 116.

Figure 1C:
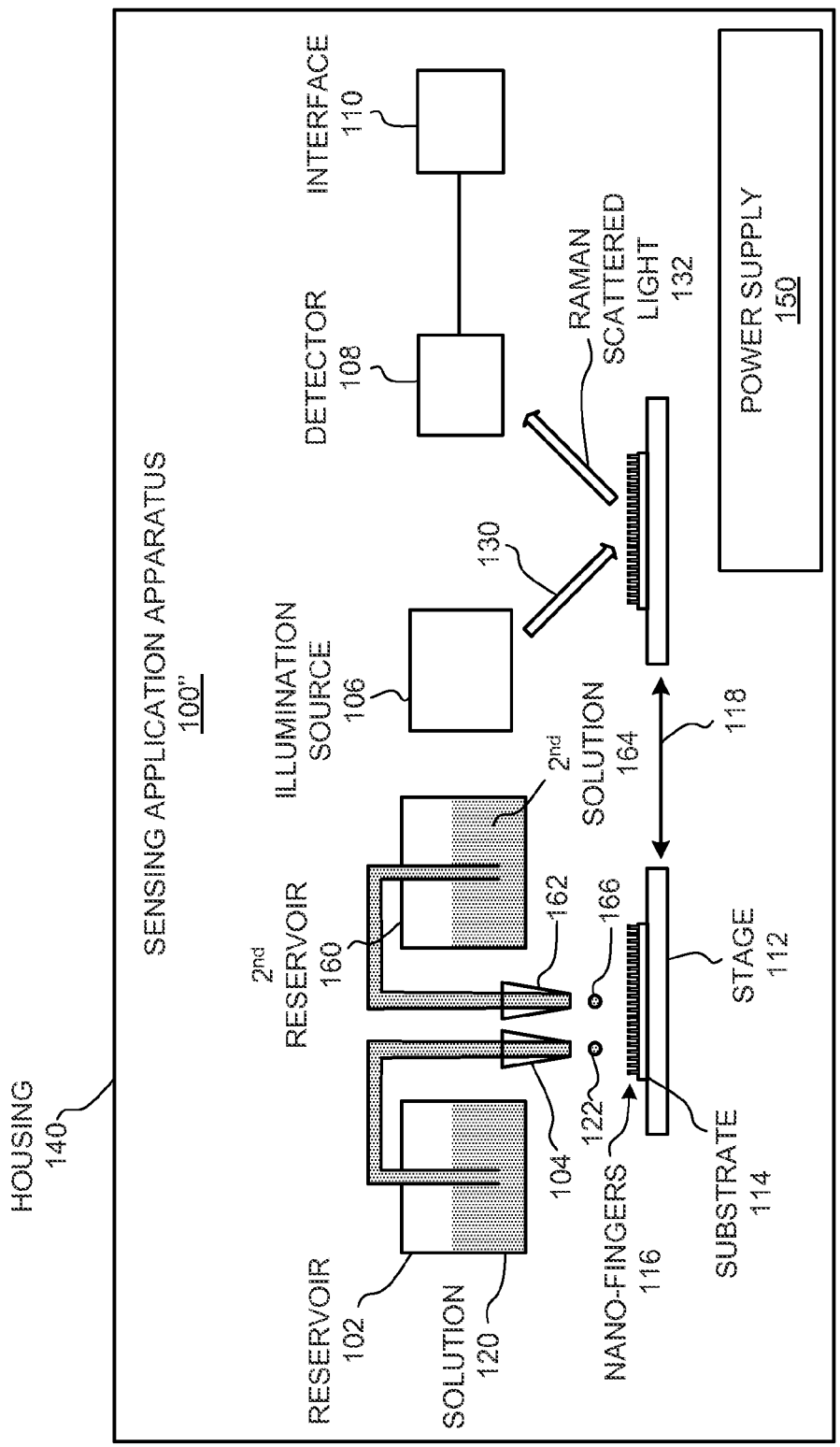

Turning now to FIG. 1C, there is shown a simplified cross-sectional side view of an apparatus 100" for performing a sensing application, according to a further example. The apparatus 100" depicted in FIG. 1C includes many of the same components as those contained in the apparatus 100 depicted in FIG. 1A. As such, only those features in FIG. 1C that differ from those of FIG. 1A are described with respect to the apparatus 100".

As shown in FIG. 1C, the sensing application apparatus 100" includes a second reservoir 160 and a second dispenser 162. The second reservoir 160 is depicted as containing a second solution 164 that is dispensed onto the substrate 114 through the second dispenser 162. The second dispenser 162 comprises any reasonably suitable type of dispenser that is to controllably dispense the second solution 162 from the second reservoir 160 onto the nano-fingers 116. The second dispenser 162 may comprise any of the types of dispensers and may be operated in any of the manners discussed above with respect to the dispenser 104, for instance, to controllably deliver a fixed volume of the second solution 164 onto the nano-fingers 116.

According to an example, the second solution 164 comprises a different composition than the solution 120 contained in the reservoir 102. In this regard, the solutions 120 and 164 may be deposited onto differently located sets of the nano-fingers 116 and testing of an analyte at the differently located sets of nano-fingers 116 may be performed. In another example, the solutions 120 and 164 may be deposited onto the same set of nano-fingers 116 by moving either or both of the stage 112 and the dispensers 104, 162. For instance, the solutions 120 and 164 may be mixed as the solutions 120 and 164 are deposited onto the nano-fingers 116 in instances where a combination of the solutions 120 and 162 is not desired or practical until an analyte is to be introduced into the apparatus 100".

Although the sensing application apparatuses 100, 100', 100" in FIGS. 1A-1C have been depicted as including either one or two reservoirs 102, 160 and either one or two dispensers 104, 162, it should be understood that the apparatuses 100, 100', 100" may include any reasonable numbers of these elements without departing from the scopes of the apparatuses 100, 100', 100". In addition, the sensing application apparatuses 100, 100', 100" may include multiple dispensers 104, 162 per reservoir 102, 160.

Figure 2A:
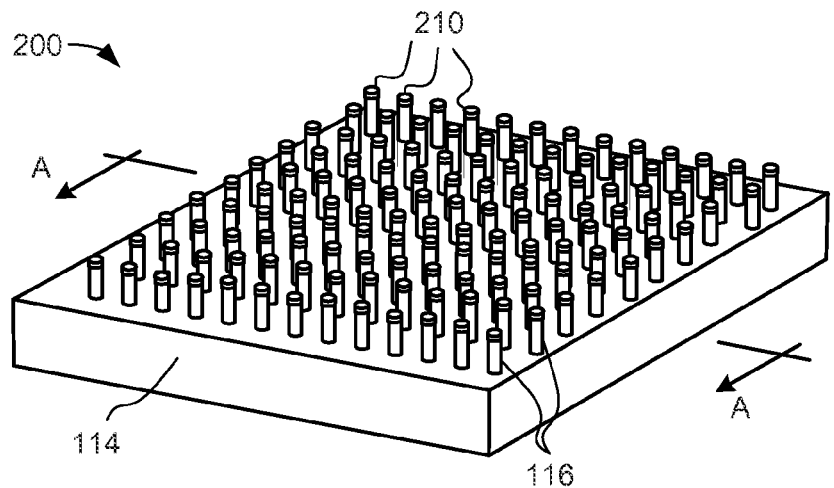
FIG. 2A shows an isometric view of an array of nano-fingers for use in a sensing application, according to an example of the present disclosure.

Turning now to FIG. 2A, there is shown an isometric view of an array 200 of the nano-fingers 116 depicted in FIGS. 1A-1C, according to an example. As shown in FIG. 2A, the array 200 includes the substrate 114 upon which the nano-fingers 116 extend. More particularly, the nano-fingers 116 are depicted as being attached to and extending above a surface of the substrate 114. The substrate 114 may be formed of any suitable material, such as, paper, silicon, silicon nitride, glass, plastic, polymer, $SiO_2$, $Al_2O_3$, aluminum, etc., or a combination of these materials, etc.

According to an example, the nano-fingers 116 are formed of a relatively flexible material to enable the nano-fingers 116 to be laterally bendable or collapsible, for instance, to enable tips of the nano-fingers 116 to move toward each other, as discussed in greater detail herein below. Examples of suitable materials for the nano-fingers 116 include polymer materials, such as, UV-curable or thermal curable imprinting resist, polyalkylacrylate, polysiloxane, polydimethylsiloxane (PDMS) elastomer, polyimide, polyethylene, polypropelene, fluoropolymer, etc., or any combination thereof, metallic materials, such as, gold, silver, aluminum, etc., semiconductor materials, etc., and combinations thereof.

The nano-fingers 116 are attached to the surface of the substrate 114 through any suitable attachment mechanism. For instance, the nano-fingers 116 are grown directly on the substrate 114 surface through use of various suitable nanostructure growing techniques. As another example, the nano-fingers 116 are integrally formed with the substrate 114. In this example, for instance, a portion of the material from which the substrate 114 is fabricated is etched or otherwise processed to form the nano-fingers 116. In a further example, a separate layer of material is adhered to the substrate 114 surface and the separate layer of material is etched or otherwise processed to form the nano-fingers 116. In various examples, the nano-fingers 116 are fabricated through a nanoimprinting or embossing process in which a template of relatively rigid pillars is employed in a multi-step imprinting process on a polymer matrix to form the nano-fingers 116. In these examples, a template may be formed through photolithography or other advanced lithography with the desired patterning to arrange the nano-fingers 110 in the predetermined arrangement. More particularly, for instance, the desired patterns may be designed on a mold, by E-beam lithography, photolithography, laser interference lithography, Focused Ion Beam (FIB), self-assembly of spheres, etc. In addition, the pattern may be transferred onto, for instance, silicon, glass, or polymer substrate (PDMS, polyimide, polycarbonate, etc.). Various other processes, such as, etching, and various techniques used in the fabrication of micro-electromechanical systems (MEMS) and nano-electromechanical systems (NEMS) may also be used to fabricate the nano-fingers 116.

The nano-fingers 116 have been depicted as having substantially cylindrical cross-sections. It should, however, be understood that the nano-fingers 116 may have other shaped cross-sections, such as, for instance, rectangular, square, triangular, etc. In addition, or alternatively, the nano-fingers 116 may be formed with one or more features, such as, notches, bulges, etc., to substantially cause the nano-fingers 116 to be inclined to collapse in particular directions. Thus, for instance, two or more adjacent nano-fingers 116 may include the one or more features to increase the likelihood that the nano-fingers 116 collapse toward each other. Various manners in which the nano-fingers 116 may be collapsed are described in greater detail herein below.

The array 200 includes a substantially random distribution of nano-fingers 116 or a predetermined configuration of nano-fingers 116. In any regard, according to an example, the nano-fingers 116 are arranged with respect to each other such that the tips of at least two neighboring nano-fingers 116 are able to be brought into close proximity with each other when the nano-fingers 116 are in a collapsed state. By way of particular example, the neighboring nano-fingers 116 are positioned less than about 100 nanometers apart from each other. According to a particular example, the nano-fingers 116 are patterned on the substrate 114 such that neighboring ones of the nano-fingers 116 preferentially collapse into predefined geometries, for instance, triangles, squares, pentagons, etc.

In addition, although FIG. 2A depicts the array as having a relatively large number of nano-fingers 116 arranged along each row, it should be understood that the array may include any number of nano-fingers 116 in each row without departing from a scope of the apparatuses 100, 100', 100". In one regard, a relatively large number of nano-fingers 116 are provided on the substrate 114 to generally enhance the likelihood of capturing molecules of an analyte to be tested as adjacent ones of the nano-fingers 116 collapse toward each other.

As also shown in FIG. 2A, Raman-active material nano-particles 210 are attached onto the tips of the nano-fingers 116. The Raman-active material nano-particles 210 comprise a Raman-active material such as, but not limited to, gold, silver, copper, platinum, aluminum, etc., or a combination of these metals in the form of alloys, or other suitable material that is able to support surface plasmons for field enhancement for Raman scattering. In addition, the Raman-active material nano-particles 210 may be multilayer structures, for example, 10 to 100 nm silver layer with 1 to 50 nm gold over-coating, or vice versa. The Raman-active material nano-particles 210 may have nanoscale surface roughness, which is generally characterized by nanoscale surface features on the surface of the layer(s) and may be produced spontaneously during deposition of the Raman-active material layer(s). By definition herein, a Raman-active material is a material that facilitates Raman scattering from a sample positioned near the Raman-active material during Raman spectroscopy.

Figure 2B:
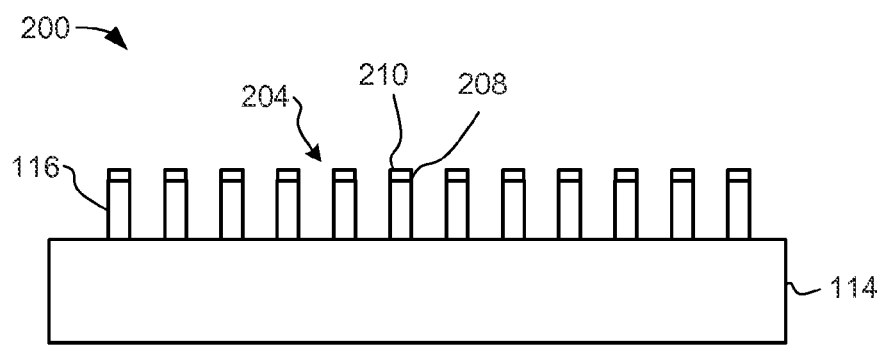
FIGS. 2B and 2C show cross-sectional views along a line A-A, of the array shown in FIG. 2A, according to examples of the present disclosure.

Turning now to FIG. 2B, there is shown a cross-sectional view along a line A-A, shown in FIG. 2A, of the array 200, in accordance with an example. As shown therein, each of the tips 208 of the nano-fingers 116 includes a respective Raman-active material nano-particle 210 disposed thereon. The Raman-active nano-particles 210 may be deposited onto the tips 208 of the nano-fingers 116 through one of, for instance, physical vapor deposition (PVD), chemical vapor deposition (CVD), sputtering, etc., of metallic material, or self-assembly of pre-synthesized nano-particles.

Although the nano-fingers 116 have been depicted in FIGS. 2A-2B as each extending vertically and at the same heights with respect to each other, it should be understood that some of the nano-fingers 116 may extend at various angles and heights with respect to each other. The differences in angles and/or heights between the nano-fingers 116 may occur, for instance, due to differences arising from manufacturing or growth variances existent in the fabrication of the nano-fingers 116 and the deposition of the nano-particles 210 on the nano-fingers 116, etc.

As shown in FIG. 2B, the nano-fingers 116 are in a first position, in which the tips 208 are in a substantially spaced arrangement with respect to each other. The gaps 204 between the tips 208 may be of sufficiently large size to enable analyte or other liquid to be positioned in the gaps 204. In addition, the gaps 204 may be of sufficiently small size to enable the tips 208 of at least some of the nano-fingers 116 to be drawn toward each other as the solution 120, 164 or other liquid evaporates, through, for instance, capillary forces applied on the tips 208 as the solution 120, 164 deposited on the nano-fingers 116 evaporates. In addition, in instances where the analyte comprises a liquid, the nano-fingers 116 may collapse toward each other through capillary forces applied on the tips 208 as the analyte evaporates.

Figure 2C:
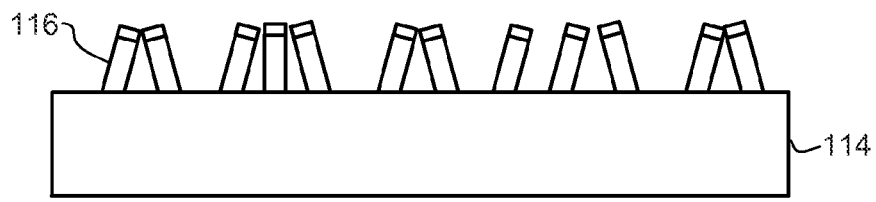

Turning now to FIG. 2C, there is shown a cross-sectional view along a line A-A, shown in FIG. 2A, of the array 200, following evaporation of the solution 120, 164 and/or the analyte. The view depicted in FIG. 2C is identical to the view depicted in FIG. 2B, except that the nano-fingers 116 are depicted in a second position, in which the tips 208 of some of the nano-fingers 116 have been drawn toward with each other. According to an example, the tips 208 of some of the nano-fingers 116 may be in and may remain in relatively close proximity to with each other for a period of time due to the capillary forces applied on adjacent ones of the nano-fingers 116 during and following evaporation of the solution 120, 164 in the gaps 204 between the tips 208.

In any event, and in one regard, the tips 208 of the nano-fingers 116 are caused to be drawn toward each other as shown in FIG. 2C to cause an analyte molecule to be tested to substantially be trapped between the Raman-active material nano-particles 210 positioned on adjacent tips 208. In this regard, a relatively small gap, for instance, a few nanometers or less, between the adjacent ones of the Raman-active material nano-particles 210 positioned on the tips 208 may remain when analyte molecules are trapped between the adjacent tips 208. By substantially trapping an analyte molecule to be tested between the Raman-active material nano-particles 210 that are in relatively close proximity to each other, SERS on the analyte molecule may be enhanced because the relatively small gaps between the Raman-active material nano-particles 210 create "hot spots" having relatively large electric field strengths. Substantially trapping an analyte molecule here is intended to indicate that the analyte molecule may either be trapped between at least two Raman-active material nano-particles 210 that are in relatively close proximity to each other or attached on one of the at least two Raman-active material nano-particles 210 that are in relatively close proximity to each other.

Figure 3:
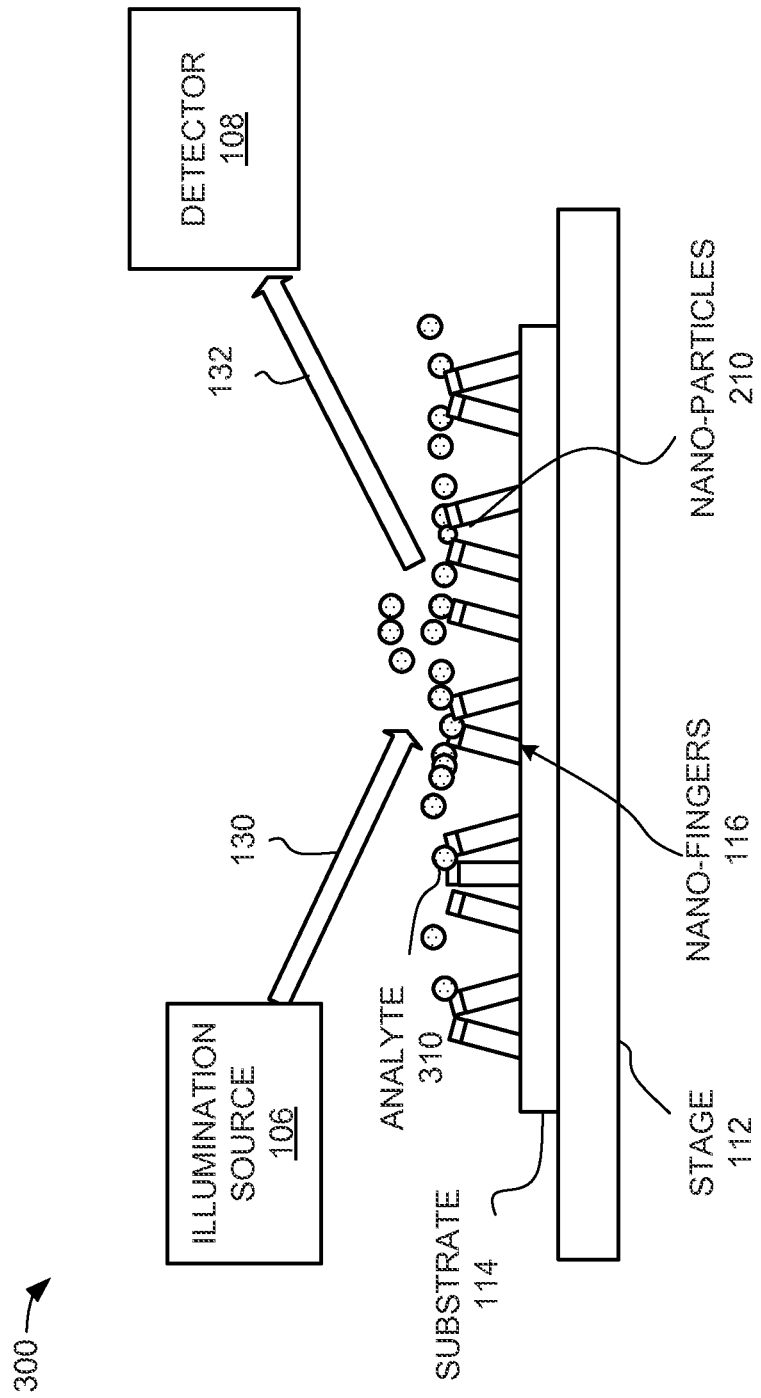
FIG. 3 shows a simplified block diagram of a sensing apparatus for use in a sensing application, according to an example of the present disclosure.

With reference now to FIG. 3, there is shown a simplified block diagram 300 of a portion of the sensing application apparatus 100 depicted in any of FIGS. 1A-1C, according to an example. Generally speaking, the block diagram 300 depicts in greater detail operations performed to illuminate and detect Raman scattered light emitted from an analyte 310.

As shown in FIG. 3, molecules of an analyte 310 to be tested are depicted as being positioned in contact with and in close proximity to the Raman-active material nano-particles 210. Some of the analyte molecules 310 are also depicted as being trapped between a couple adjacent ones of the Raman-active material nano-particles 210. According to an example, the illumination source 106 is to direct a beam of illumination 130 to locations of different subsets of the nano-particles 210 to thereby enable testing to be performed on the various locations of the Raman-active material nano-particles 210. The placement of the beam of illumination 130 may be changed through any of a variety of different manners. For instance, the direction of the beam of illumination 130 may be varied by changing an angle at which the beam is emitted from the illumination source 106. As another example, a movable mirror may be implemented to vary the direction in which the beam of illumination 130 is directed. As a further example, the stage 112 may be moved with respect to the beam of illumination 130.

In any regard, the beam of illumination 130 illuminates the molecules of the analyte 310 and the Raman-active material nano-particles 210. Illumination of the Raman-active material nano-particles 210 causes hot spots of relatively large electric field strength to occur. The hot spots are increased at the locations where the Raman-active material nano-particles 210 are in relatively close proximity to each other, for instance, within a few nanometers, or are in contact each other. The electric fields generated between the Raman-active material nano-particles 210 that are in relatively close proximity to each other generally enhance the rate at which Raman light is scattered by the analyte molecules 310 positioned at or near the contact locations. The Raman scattered light, which is represented by the arrow 132, is shifted in frequency by an amount that is characteristic of particular vibrational modes of the analyte molecules 310. The detector 108 is to collect the Raman scattered light 132 and spectral analysis is to be performed on the collected Raman scattered light 132 either at the apparatus 100, 100', 100" or at a device external to the apparatus 100, 100', 100".

Although the Raman scattered light 132 has been depicted as being directed toward the detector 108, the Raman scattered light 132 is emitted in multiple directions. In this regard, some of the Raman scattered light 132 may be directed into the stage 112, which, in one example, comprises an optical waveguide. In addition, the illumination source 106 may cause the beam of illumination 130 to be directed into the stage 112. In this example, Raman scattered light 132 may be generated in the stage 112 as a result of the analyte 310 coupling to an evanescent field of a waveguide mode generated by the illumination 130 being emitted through the stage 112. In addition, the detector 108 may be positioned to detect the waves generated in the stage 112 from the Raman scattered light 132. In any regard, the detector 108 may include a filter to filter out light originating from the illumination source 106, for instance, through use of a grating-based monochrometer or interference filters. The detector 108 may alternatively be positioned at other locations with respect to the nano-fingers 116, for instance, below the stage 112 in FIG. 3.

The detector 108 is generally to convert the detected Raman scattered light 132 into electrical signals. In some examples, the detector 108 is to output the electrical signals to other components (not shown) that are to process the electrical signals, such as, a computing device, through the interface 110. In other examples, the detector 108 is equipped with the processing capabilities.

Figure 4:
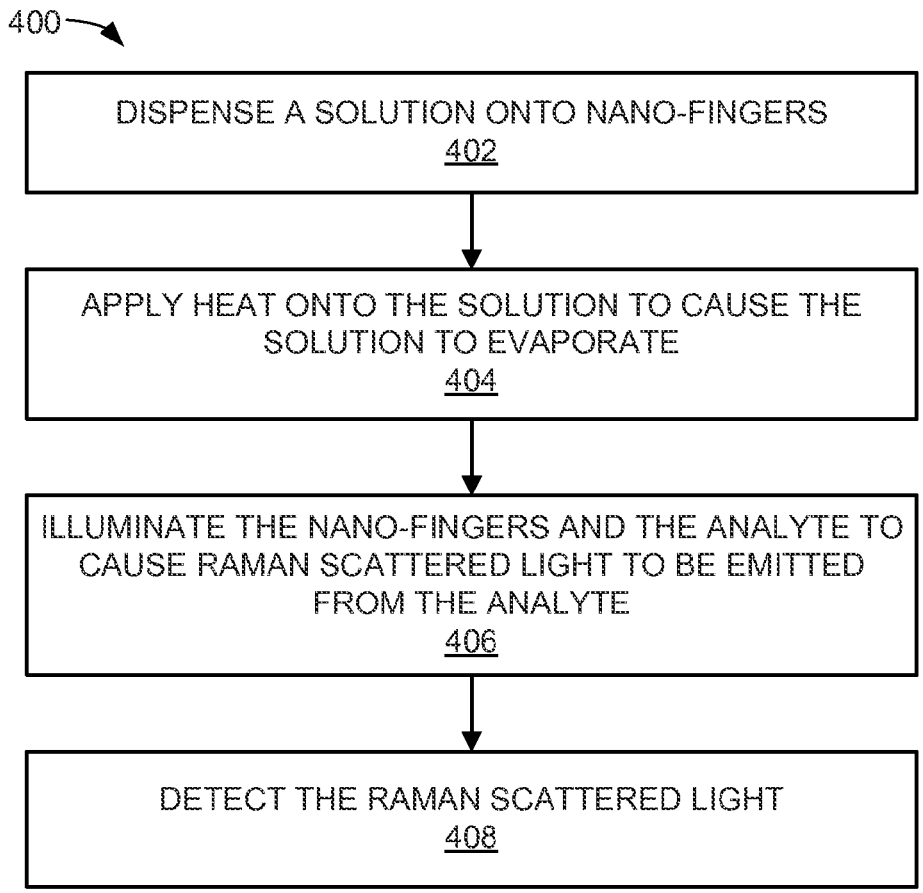
FIG. 4 shows a flow diagram of a method for performing a sensing application on an analyte introduced onto a plurality of nano-fingers, according to an example of the present disclosure.

Turning now to FIG. 4, there is shown a flow diagram of a method 400 for performing a sensing application on an analyte 310 introduced onto a plurality of nano-fingers 116, according to an example. It should be understood that the method 400 may include additional operations and that some of the processes described herein may be removed and/or modified without departing from a scope of the method 400.

Prior to or during implementation of the method 400, the analyte 310 may be introduced onto the nano-fingers 116 either directly or indirectly. By way of example, the analyte 310 may be mixed with the solution 120 prior to dispensing of the solution/analyte mix onto the nano-fingers 116. As another example, the analyte 310 may be contained in a second reservoir 160 and may be delivered onto the nano-fingers 116 by a second dispenser 162 in fluid communication with the second reservoir 160. As a further example, the analyte 310 may be present in the ambient environment around the sensing application apparatus 100, 100', 100" and may be introduced through an opening in the housing 140 of the sensing application apparatus 100, 100', 100". The analyte 310 may alternatively be introduced in various other manners.

At block 402, a solution 120 from a reservoir 102 is dispensed onto the nano-fingers 116. As discussed above, a dispenser 104 in fluid communication with the reservoir 102 is operated to controllably dispense the solution 120 onto the nano-fingers 116. Thus, for instance, the dispenser 104 may be operated to dispense the solution 120 onto a predefined subset of the nano-fingers 116. In addition, or alternatively, the dispenser 104 may be operated to dispense a predetermined volume of the solution 120 onto the nano-fingers 116.

At block 404, heat is applied onto the solution to cause the solution to evaporate. Heat may also be applied onto the analyte at block 404. In one example, the heat is applied by the illumination source 106. In this regard, the illumination source 106 performs both functions of evaporating the solution 120 and illuminating the analyte 310. In another example, the heat is applied by a separate heating element (not shown), for instance, a heating element, such as a resistor, provided in the stage 112 that applies heat onto the substrate 114 and the nano-fingers 116. The separate heating element may also comprise, for instance, a separate light source, the power supply 150, etc.

In any regard, and as discussed above, the nano-fingers 116 are positioned sufficiently close to each other to cause at least some of the nano-fingers 116 to be drawn toward each other as the solution 220 (and the analyte 310) evaporates due to capillary forces applied onto the nano-fingers 116. In addition, in instances where the analyte 310 is present during the drawing together of the nano-fingers 116, portions of the analyte 310 are likely to be trapped between and/or positioned adjacent to the adjacent tips or the Raman-active material nano-particles 210 positioned on the tips.

At block 406, the nano fingers 116 and the analyte 310 are illuminated by the illumination source 106 to cause Raman scattered light 132 to be emitted from the analyte 310. As discussed above, the Raman active nano-particles 210 provided on the tips of the nano-fingers 116, and particularly the Raman active nano-particles 210 that are in relatively close proximity to or in contact with each other, enhance the production of Raman scattered light 132 from the analyte 310 by concentrating or otherwise enhancing an electromagnetic field in or around the analyte 310.

At block 408, the Raman scattered light is detected by the detector 108.

According to an example, the method 400 is repeated a number of times to detect Raman scattered light 132 emitted from portions of the analyte 310 positioned on different subsets of the nano-fingers 116. In this example, the positions at which the portions of the analyte 310 may be varied between each iteration of the method 400 through manipulation of at least one of the positions of the stage 112 and the location at which the beam of illumination 130 illuminates the nano-fingers 116. In addition, and according to an example, the different subsets of nano-fingers 116 at which the portions of the analyte 310 are tested may have received different types of solutions 120, 164 at block 402. In this example, and as shown in FIG. 1C, different solutions 120, 164 may be dispensed onto different subsets of nano-fingers 116 by different dispensers 104, 162. As such, for instance, different solutions 120, 164 that interact differently with an analyte 310 and/or different types of analytes 310 may be deposited onto different subsets of nano-fingers 116 and tested during subsequent iterations of the method 400.

Figure 5:
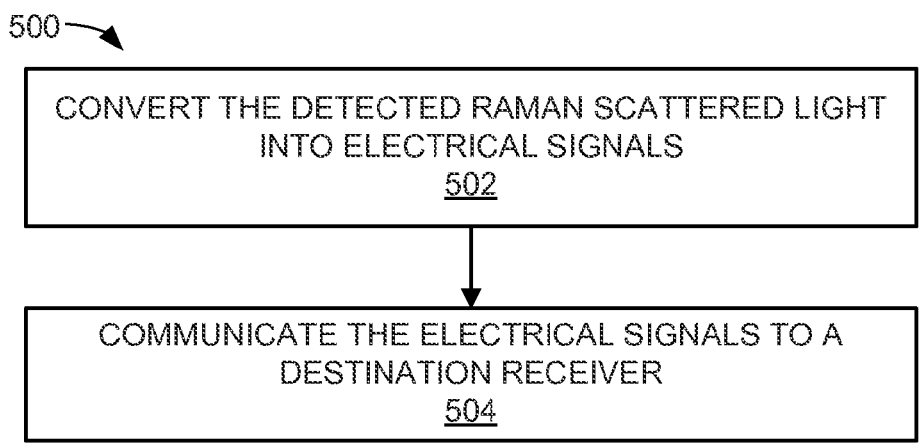
FIG. 5 shows a flow diagram of a method for communicating electrical signals representative of the detected Raman scattered light to a destination receiver, according to an example of the present disclosure

Turning now to FIG. 5, there is shown a flow diagram of a method 500 for communicating electrical signals representative of the detected Raman scattered light to a destination receiver, according to an example. It should be understood that the method 500 may include additional processes and that some of the processes described herein may be removed and/or modified without departing from a scope of the method 500.

At block 502, the Raman scattered light detected at block 408 is converted into electrical signals. In addition, at block 504, the electrical signals are communicated to a destination receiver, for instance, through the interface 110. As discussed above, the interface 110 may comprise a wireless interface through which the electrical signals are wirelessly communicated to the destination receiver. According to a particular example, the interface 110 is to a cloud environment and the electrical signals are submitted to the cloud environment for retrieval and processing by a processing device, such as, a computer, a server, etc.

Some or all of the operations set forth in the methods 400 and 500 may be contained as a utility, program, or subprogram, in any desired computer accessible medium. In addition, the methods 400 and 500 may be embodied by machine readable instructions, which may exist in a variety of forms both active and inactive. For example, they may exist as source code, object code, executable code or other formats. Any of the above may be embodied on a non-transitory computer readable storage medium. Examples of non-transitory computer readable storage media include conventional computer system RAM, ROM, EPROM, EEPROM, and magnetic or optical disks or tapes. It is therefore to be understood that any electronic device capable of executing the above-described functions may perform those functions enumerated above.

Figure 6:
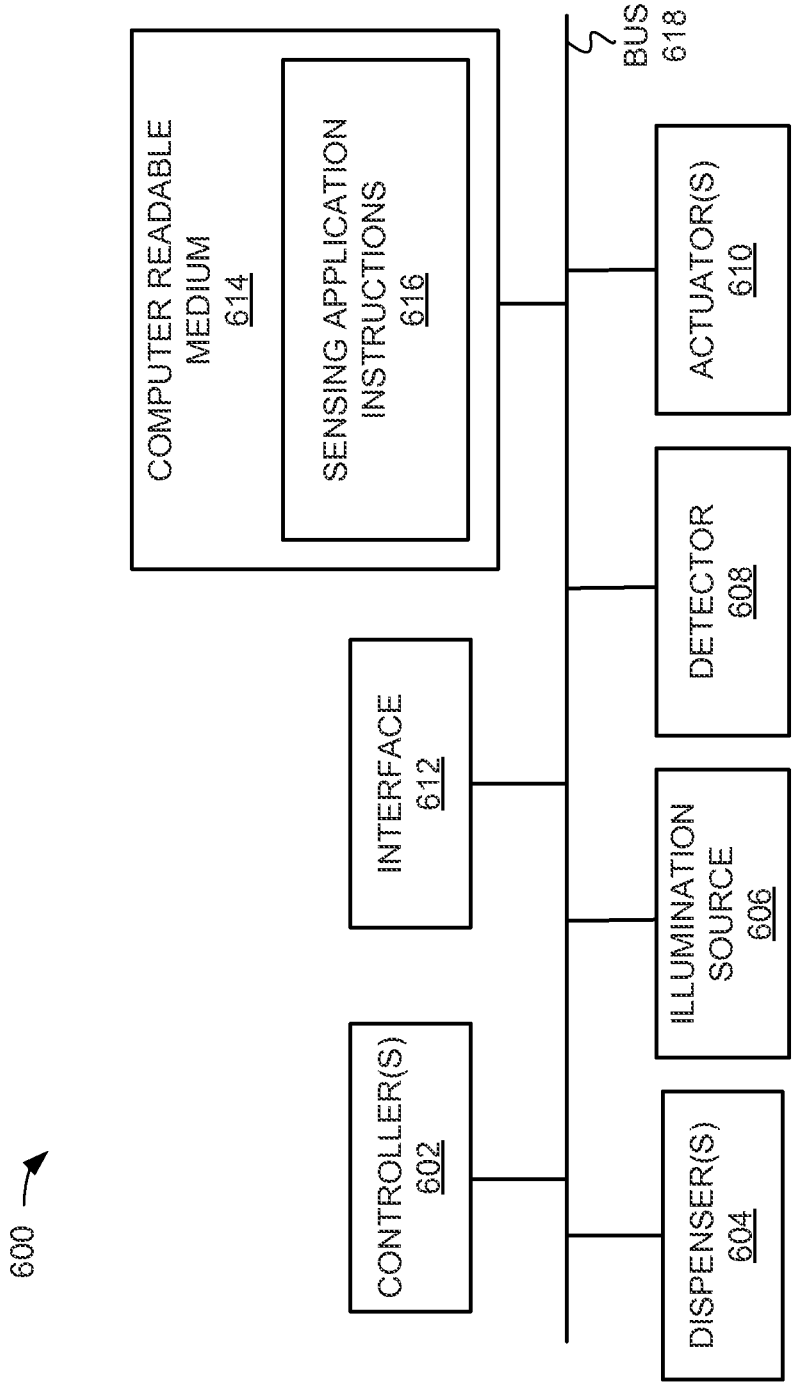
FIG. 6 illustrates a schematic representation of a sensing application apparatus, such as any of the sensing application apparatuses depicted in FIGS. 1A-1C, according to an example of the present disclosure.

Turning now to FIG. 6, there is shown a schematic representation of a sensing application apparatus 600, such as any of the sensing application apparatuses 100, 100', 100" depicted in FIGS. 1A-1C, according to an example. The apparatus 600 includes a controller 602, such as a processor, an ASIC, etc. The controller 602 is depicted as being in communication with a dispenser 604, an illumination source 606, a detector 608, an actuator 610, an interface 612, and a computer readable medium 614 over a bus 618. For example, the bus 618 may be an EISA, a PCI, a USB, a FireWire, a NuBus, or a PDS. Although not shown, the apparatus 600 may include additional components, such as, a display, input interface, etc., through which a user may input instructions and/or receive information.

The computer readable medium 614 comprises any suitable medium that participates in providing instructions to the controller 602 for execution. For example, the computer readable medium 614 may be non-volatile media. As shown in FIG. 6, the computer readable medium 614 stored thereon a set of sensing application instructions 616.

The set of sensing application instructions 616 includes a set of machine readable instructions for controlling operation of the apparatus 600 components in implementing the methods 400 and 500 respectively depicted in FIGS. 4 and 5. The sensing application instructions 616 may thus comprise instructions to control the dispenser 604 to dispense a solution 120 onto the nano-fingers 116, to control the illumination source 606 to apply heat onto the solution 122, to control the illumination source 606 to illuminate the nano-fingers 116 and portions of an analyte, to control the detector 608 to detect Raman scattered light emitted from the analyte, and to control the actuator(s) 610 to vary at least one of a position of the substrate 114 and a beam of illumination 130 emitted from the illumination source 130. In addition, the sensing application instructions 616 may also include machine-readable instructions to control the detector 608 to convert the detected Raman scattered light into electrical signals and to communicate the electrical signals to a destination receiver.

In certain examples, the processes may be at least partially implemented in digital electronic circuitry, or in computer hardware, machine readable instructions (including firmware and software), or in any combination thereof, as also discussed above.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. An apparatus for performing a sensing application, said apparatus comprising:
   a reservoir to contain a solution;
   a dispenser to dispense the solution from the reservoir;
   a substrate having a plurality of nano-fingers positioned to receive the dispensed solution, wherein the plurality of nano-fingers are flexible, such that the plurality of nano-fingers are configurable with respect to each other;
   an illumination source to illuminate the received solution, an analyte introduced around the plurality of nano-fingers, and the plurality of nano-fingers, wherein light is to be emitted from the analyte in response to being illuminated; and
   a detector to detect the light emitted from the analyte;

wherein the dispenser is to dispense the solution onto a subset of the plurality of nano-fingers, and wherein the plurality of nano-fingers are positioned in sufficiently close proximity to each other to cause the subset of the plurality of nano-fingers to collapse toward each other as the solution evaporates through application of capillary forces onto the plurality of nano-fingers in the subset by the solution.

2. The apparatus according to claim 1, wherein the plurality of nano-fingers comprise respective tips, said apparatus further comprising:
Raman-active material nano-particles attached to respective tips of the plurality of nano-fingers.

3. The apparatus according to claim 2, wherein the plurality of nano-fingers are to be collapsed toward each other such that the Raman-active material nano-particles attached to the respective tips of subsets of the plurality of nano-fingers are brought into close proximity or in contact with each other.

4. The apparatus according to claim 1, further comprising:
a heating element to increase the rate at which the solution evaporates.

5. The apparatus according to claim 1, wherein the illumination source is to apply heat to the solution on the subset of the plurality of nano-fingers to substantially enhance evaporation of the solution.

6. The apparatus according to claim 1, further comprising:
a movable stage; and
wherein the substrate is positioned on the movable stage, and wherein the movable stage is to be moved from a location to receive the solution from the dispenser to a location to be illuminated by the illumination source.

7. The apparatus according to claim 1, wherein the detector is to generate signals representative of the detected light, said apparatus further comprising:
a wireless interface to wirelessly communicate the signals to a destination receiver that is externally located with respect to a housing of the apparatus.

8. The apparatus according to claim 1, further comprising:
a second reservoir to contain a second solution; and
a second dispenser to dispense the second solution from the reservoir onto a second subset of the plurality of nano-fingers that differs from a subset of the plurality of nano-fingers onto which the dispenser is to dispense the solution from the reservoir, wherein the illumination source is to further illuminate the dispensed second solution and wherein the detector is to detect light emitted from an analyte introduced around the second subset of the plurality of nano-fingers.

9. The apparatus according to claim 1, further comprising:
a housing that encapsulates the reservoir, the dispenser, the substrate, the illumination source, and the detector, wherein the housing is sized for handheld use.

10. A method for performing a sensing application on an analyte introduced onto a plurality of nano-fingers, said method comprising:
dispensing, from a reservoir, a solution onto the plurality of nano-fingers, wherein Raman-active material nano-particles are attached to respective tips of the plurality of nano-fingers;
applying heat onto the solution to cause the solution to evaporate, wherein evaporation of the solution causes tips of adjacent ones of the plurality of nano-fingers to be drawn toward each other through capillary forces applied on the tips by the solution, and wherein molecules of the analyte are at least one of trapped between and positioned adjacent to the Raman-active material nano-particles attached to the respective tips that have been drawn toward each other;
illuminating the Raman-active material nano-particles and the analyte to cause enhanced Raman scattered light to be emitted from the analyte; and
detecting the enhanced Raman scattered light.

11. The method according to claim 10, further comprising:
converting the detected Raman scattered light into electrical signals; and
wirelessly communicating the electrical signals.

12. The method according to claim 10, wherein illuminating the plurality of nano-fingers further comprises illuminating the plurality of nano-fingers with an illumination source, and wherein applying heat onto the solution further comprises applying heat from the illumination source.

13. The method according to claim 10, said method further comprising:
dispensing, from a second reservoir, a second solution onto a second subset of the plurality of nano-fingers, wherein applying heat onto the solution further comprises applying heat onto the second solution;
illuminating the Raman-active nano-particles and the analyte around the second subset of the plurality of nano-fingers to cause enhanced Raman scattered light to be emitted from the analyte near the second subset of the plurality of nano-fingers; and
detecting the enhanced Raman scattered light emitted from the analyte near the second subset of the plurality of nano-fingers.

14. A non-transitory computer readable storage medium on which is stored machine readable instructions, that when executed by a processor are to implement a method for performing a sensing application on an analyte introduced onto a plurality of nano-fingers, said machine readable instructions comprising code to:
dispense, from a reservoir, a solution onto the plurality of nano-fingers, wherein Raman-active material nano-particles are attached to respective tips of the plurality of nano-fingers;
apply heat, by an illumination source, onto the solution to cause the solution to evaporate, wherein evaporation of the solution causes tips of adjacent ones of the plurality of nano-fingers to be drawn toward each other through capillary forces applied on the tips, and wherein molecules of the analyte are at least one of trapped between and positioned adjacent to the Raman-active material nano-particles that are attached to the respective tips that have been drawn toward each other;
illuminate, by the illumination source, the Raman-active material nano-particles and the analyte to cause Raman scattered light to be emitted from the analyte;
detect, by a detector, the Raman scattered light;
convert the detected Raman scattered light into electrical signals; and
communicate the electrical signals to a destination receiver.

* * * * *